United States Patent [19]

Spooner et al.

[11] Patent Number: 4,697,463

[45] Date of Patent: Oct. 6, 1987

[54] METHOD OF AND MEANS FOR TESTING FLOW PROPERTIES OF MAGNETIC TONERS

[75] Inventors: Anthony N. Spooner, Vale Park; Luis Lima-Marques, Bedford Park, both of Australia

[73] Assignee: Research Laboratories of Australia Pty. Ltd., Australia

[21] Appl. No.: 770,868

[22] PCT Filed: Mar. 12, 1984

[86] PCT No.: PCT/AU84/00248

§ 371 Date: Aug. 6, 1985

§ 102(e) Date: Aug. 6, 1985

[87] PCT Pub. No.: WO85/02678

PCT Pub. Date: Jun. 20, 1985

[30] Foreign Application Priority Data

Dec. 9, 1983 [AU] Australia .............................. PG2781

[51] Int. Cl.⁴ ...................... G01N 11/02; G01N 27/74
[52] U.S. Cl. ...................................... 73/866; 73/432.1; 324/204; 324/226; 355/3 DR
[58] Field of Search ........ 324/200, 226, 204, 214–216; 355/3 DR; 73/54–59, 64, 432.1, 866; 29/116 R; 118/657, 658, 712, 713

[56] References Cited

U.S. PATENT DOCUMENTS 3,771,352 11/1973 Powell et al. ............................ 73/54
4,047,814 9/1977 Westcott ............................ 73/64 X
4,142,281 3/1979 Muller ............................ 29/132 X
4,412,176 10/1983 Kramer et al. ...................... 324/204
4,602,863 7/1986 Fritz et al. ...................... 118/658 X Primary Examiner—Gerard R. Strecker
Attorney, Agent, or Firm—Kinzer, Plyer, Dorn, McEachran & Jambor

[57] ABSTRACT

A method for testing electrostatic developer toners which comprises applying the toner to a stationary non-magnetic sleeve (4), moving the toner along the surface of the sleeve by an array of field lines generally normal to the surface produced by a multiple magnetic roll (1) rotating within the sleeve and determining the characteristics of the toner from the pattern (15) of the spread toner by reference to a calibrated scale (9) and a stop line (5) on the surface of the sleeve.

5 Claims, 2 Drawing Figures

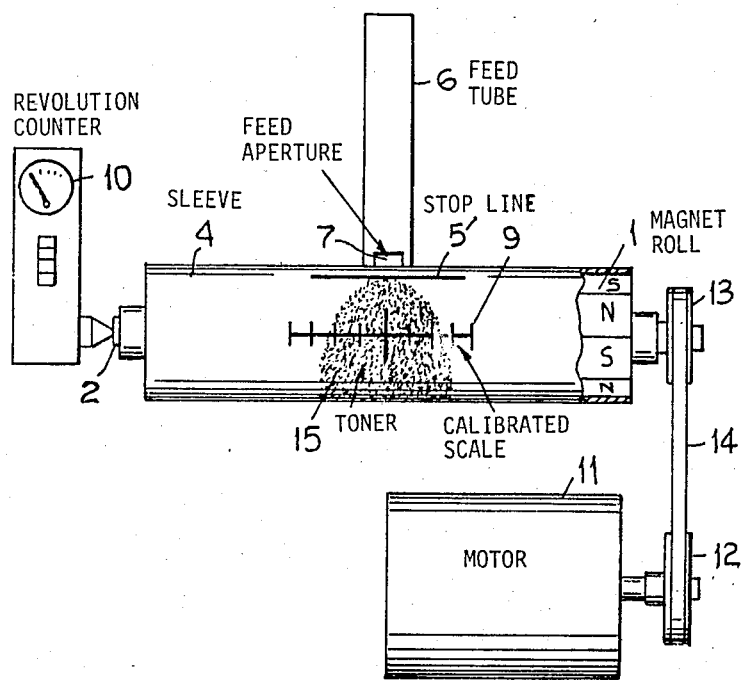
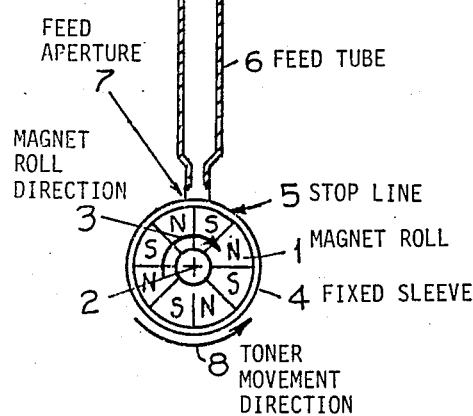

METHOD OF AND MEANS FOR TESTING FLOW PROPERTIES OF MAGNETIC TONERS

BACKGROUND OF THE INVENTION

It is well known to tone electrostatic latent images contained on photoconductive or dielectric surfaces by application thereto of so called monocomponent or single component electroscopic marking particles or toner which may be of the heat fixing or cold pressure fixing type.

Single component toner particles contain magnetisable material such as for instance magnetite whereby such toner can be applied for toning purposes to the latent image bearing surface by means of a magnetic applicator roll. It is customary to have the single component toner contained within a hopper or tank from which it is fed onto the applicator roll. The applicator roll consists usually of a non magnetic stationary or rotating sleeve within which is contained a rotating multi-pole magnet roll. As such magnet roll rotates, the magnetic field lines associated with the poles usually of alternating polarity attract toner to the non-magnetic outer sleeve and cause said toner to form a coating thereon, commonly referred to as the magnetic brush. A so called doctor blade is usually fitted to control the coating thickness or the height of the magnetic brush. The magnetic brush is brought into close proximity to the latent image bearing surface to effect toner transfer over the so called toning gap by attraction to the latent image areas where the electrostatic forces associated therewith overcome the magnetic forces holding the toner against the sleeve of the applicator roll.

The machine performance that is image quality and stability of single component toners depends on a number of properties of the toner material such as electrical conductivity, tribocharging characteristics, particle size and particle size distribution, etc., as is well known in the art. One of the main factors affecting machine performance of the toner is related to its flow properties as is also well known. By good flow properties is meant the ability of the toner to distribute itself uniformly and rapidly over the surface of the outer sleeve of the magnetic applicator roll so that imagewise removed toner material by the latent image bearing surface is instantly replenished and thus the magnetic brush in the toning gap is of constant height and uniformity. Poor flow properties of a toner are indicated by uneven image density mainly in the form of streaks or bands along the copy, which are caused by uneven toner distribution on the applicator roll or insufficient toner in localised portions thereof.

In order to improve the flow properties of single component toners it is customary to admix so-called flow improvers such as silica powders and the like therewith in certain specific proportions.

A common test of toner flow characteristics is measurement of the angle of repose of the toner. However such measurement can give widely varying results in repeat testing of one and the same sample due to variation in degree of aeration, amongst other things, and the test results thus obtained can not be directly related to actual machine performance.

OBJECT OF THE INVENTION

The object of this invention is to provide a method of and means for testing or measuring at least on a comparative basis in a reproducible manner the flow properties of magnetic toners where such flow properties as determined in accordance with this invention can be readily correlated with the flow of the toner on a magnetic applicator roll in actual machine operation.

The novel apparatus or test device in accordance with this invention comprises in essence a multi-pole magnet member mounted in such manner that relative motion between the magnet member and a toner support at a predetermined speed results, the toner support being associated with a toner metering feed tube and scales measuring the rate at which the toner spreads over or coats the support.

In its preferred form the apparatus for testing flow properties of magnetic toners consists in essence of a cylindrical non-magnetic stationary sleeve, a rotatably mounted multi-pole magnet roll contained within said stationary sleeve, means to rotate said magnet roll at predetermined speeds, means adapted to feed a predetermined quantity of magnetic toner onto the surface of said stationary sleeve, markings contained on the surface of said stationary sleeve adapted to define the circumferential and axial spread thereon of said predetermined quantity of magnetic toner fed thereto and means to count the number of revolutions of said multi-pole magnet roll in relation to the spread of said predetermined quantity of magnetic toner as defined by said markings. The method of testing electrostatic developer toners comprises applying the toner to the surface of a toner support and moving it along the support and recording the pattern of movement and is characterised by applying the toner to one surface of the support, producing an array of magnetic field lines in a direction generally normal to the field lines, and determining the characteristics of the toner from the pattern of the toner particles spread along the surface of the toner support under influence of the relative movement the toner support surface and the magnetic field lines.

BRIEF DESCRIPTION OF THE DRAWINGS

FIG. 1 is a sectional side elevation of a preferred embodiment showing the rotating multipole magnet, fixed sleeve and toner feed tube.

FIG. 2 is a front elevation of the fixed sleeve and toner feed tube showing the spread scale, drive mechanism and revolution counter, the fixed sleeve being part sectioned.

DESCRIPTION OF THE PREFERRED EMBODIMENT

Referring now to FIG. 1 in detail, multi pole magnet roll 1, is mounted on axle 2 and arranged to revolve in the direction shown by arrow 3. The multi-pole magnet roll 1 is enclosed in stationary sleeve 4, stationary sleeve 4 has stop line 5 inscribed thereon. The toner feed tube 6 is mounted vertically above and normal to fixed sleeve 4, and spaced apart therefrom to form a feed aperture 7. When toner is fed into toner feed tube 6 and allowed to flow through feed aperture 7, rotation of multi-pole magnet roll 1 in the direction shown causes toner to travel around fixed sleeve 4 in the direction shown by arrow 8.

Referring now to FIG. 2 in detail, multi-pole magnet 1 of FIG. 1 is mounted on axle 2 and enclosed in fixed sleeve 4. Toner feed tube 6 is mounted vertically by means not shown above and normal to fixed sleeve 4 to define toner feed aperture 7. Stop line 5 is engaged in the position shown on fixed sleeve 4. Calibrated spread scale 9 is engraved in the position shown on fixed sleeve 4. Revolution counter 10 is frictionally engaged to one end of axle 2, and axle 2 is rotated by being driven by motor 11 through pulleys 12 and 13 and drive belt 14, thus rotating multi-pole magnet roll 1 of FIG. 1. Curved zone 15 represents the position of a toner coating formed on sleeve 4 when this apparatus is used in the manner as hereinafter described.

In a preferred embodiment of an apparatus constructed in accordance with FIGS. 1 and 2, the fixed sleeve is an aluminium tube 30 mm outside diameter, 0.5 mm wall thickness, 110 mm long. The fixed sleeve encloses a multi pole magnet roll 28.5 mm outside diameter and 110 mm long, having 8 poles symmetrically placed, alternating polarity. The magnetic strength is 1000 gauss maximum measured at the surface of the fixed sleeve.

The toner feed tube is also of aluminium, 8 mm inside diameter and 55 mm long. The toner feed aperture is cut into the lower end of the feed tube in both front and rear section, and is of rectangular cross section 5 mm wide and 2 mm high. The stop line is inscribed on the sleeve at a distance of 7 mm from the vertical axis thereof. The spread scale as shown in FIG. 2 comprises eight 5 mm divisions, that is 40 mm overall. The multi-pole magnet roll is rotated at a fixed speed, normally 270 rpm.

Prior to conducting a test, the toner sample is normalized by storing for at least 24 hours at 20° C. and 50% relative humidity. The tests are carried out under these same ambient conditions. For the test, a fixed weight of toner is introduced into the feed aperture through the feed tube and the motor is switched on. A convenient quantity of toner is 70 milligrams, but more or less may be used as desired. The motor is switched off when the leading edge of the toner coating reaches the stop line. The number of revolutions is read from the revolution counter and the spread is measured in terms of the total lateral width of the coating, in this instance about 25 mm as shown in FIG. 2.

In interpreting the test results, it can be said in general terms that the better the flow properties are of a toner, the less number of revolutions will be required to reach the stop line and the greater will be the spread during these revolutions. Typically we have found in correlation with performance is a wide range of machines, that toners having good flow properties reach the stop line within 18 and 22 revolutions. Toners with excellent flow properties reach the stop line in 17 or less revolutions, whereas toners with poor flow properties need 24 or more revolutions to reach the stop line. The total lateral spread of good toners is about 24 to 28 mm, that of toners with excellent flow properties is over 28 mm, whereas the spread of toners having poor flow properties is 24 mm or less.

It will be realised that the flow properties of a toner depend on certain fixed characteristics thereof, such as magnetite content, frictional electrification particularly of low conductivity toners, particle size distribution, particularly proportion of fines and mean particle size, also particle morphology, that is surface topography.

In addition the flow properties can be affected by variables such as moisture content, which again depends on the physical and chemical properties of the toner and appears to reach a constant level specific to particular toners after 24 hours of conditioning as referred to in the foregoing. Thus the figures given above of revolutions and spread apply to test conditions as stated earlier, that is 20° C. and 50% relative humidity.

Tests can be conducted of course under other ambient condition however the results will be different from those given here and will have to be interpreted accordingly.

We have found in general that there is a close correlation between the number of revolutions as measured in accordance with this invention and the capability of the toner in actual machine operation to move under the doctor blade for replenishing the magnetic brush on the applicator roll, whereas good spread in accordance with the test procedure of this invention correlates to the ability of the toner in actual machine operation to replenish the magnetic brush on the applicator roll in lateral direction that is along its axis.

There has been described a method of and means for testing flow properties of magnetic toners. The test results obtainable in accordance with this invention can be directly related to machine performance and can serve the purpose of assessing and comparing toners for suitability in specific applications. Configuration of test apparatus and operational data thereof found satisfactory in context of this invention have been disclosed in detail, however such detail disclosure should be construed only in illustrative rather than restrictive sense because departures therefrom by one skilled in the art could equally well serve the desired purpose without departing from the spirit of this invention.

We claim:

1. Apparatus for testing flow properties of magnetic toners consisting essentially of: a cylindrical non-magmetic stationary sleeve, a rotatably mounted multi-pole magnet roll contained within said stationary sleeve, means to rotate said magnet roll at predetermined speeds, means adapted to feed a predetermined speeds, means adapted to feed a predetermined quantity of magnetic toner onto the surface of said stationary sleeve while the magnet roll is rotated through a predetermined number of turns, markings contained on the surface of said stationary sleeve by which to observe dimensions of the circumferential and axial spread thereon of said predetermined quantity of magnetic toner fed thereto during said predetemined number of turns, where such spread is caused by the rotation of said multi-pole magnet roll during feeding of the toner and wherein the direction of such circumferential spread is opposite to the direction of rotation of said magnet roll, means to count the number of revolutions of said multi-pole magnet roll in relation to the spread of said predetermined quantity of magnetic toner as defined by said markings, whereby to determine the flow properties of the said toner.

2. Apparatus for testing flow properties of magnetic toners as in claim 1, further characterized by said multipole magnet roll being of symmetrical construction comprising an equal number of alternating magnet poles of at least 800 gauss total magnetic strength as measured on the surface of said stationary cylindrical non-magnetic sleeve.

3. Apparatus for testing flow properties of magnetic toners as in claim 1, further characterized by said means adapted to feed a predetermined quantity of magnetic toner onto the surface of said stationary sleeve being located a small distance above the uppermost center line thereof, whereby circumferential spread of said magnetic toner around said stationary sleeve is caused to commence at said uppermost center line and towards one side thereof in a direction opposite to the direction of rotation of said magnet roll and to continue towards a marking out the surface of said sleeve defining circumferential spread of said magnetic toner, and whereby axial spread of said magnetic toner is caused to commence also at said uppermost center line of said stationary sleeve and to continue concurrently with the circumferential spread of said magnetic toner within markings on the surface of said sleeve defining axial spread of said magnetic toner.

4. Apparatus for testing flow properties of magnetic toners as in claim 3, further characterized by said marking on the surface of said stationary sleeve defining the circumferential spread of said magnetic toner being located near said uppermost center line of said stationary sleeve but on that side thereof which is opposite to the side towards which circumferential spread of said magnetic toner commences whereby said marking defines a circumferential spread of said magnetic toner over a distance nearly equivalent to the circumference of said stationary sleeve, and said markings on the surface of said stationary sleeve defining the axial spread of said magnetic toner being located on the same side of said stationary sleeve which contains said marking defining the circumferential spread of said magnetic toner near the uppermost center line thereof.

5. The method of testing flow properties of magnetic toners which comprises applying the toner to the surface of a non-magnetic support and moving it along said support and recording the pattern of movement, characterised by the steps of applying the toner to one surface of a cylindrical non-magnetic support and producing by a magnetic roll rotating inside the support an array of magnetic field lines across the support alternating progressively in polarity, rotating the roll while applying toner to said support from an aperture in a container containing a measured weight of toner thereby causing relative movement between the said support and the array of magnetic field lines in a direction generally normal to the field lines whereby the toner is spread circumferentially about the support in a patten, and counting the number of turns of the roll and measuring the circumferential length and axial length of the pattern of toner on the support produced during said counted turn thereby determining the characteristics of the toner from the pattern of the toner particles spread along the surface of the support under influence of the relative movement between the surface and the magnetic field lines.

* * * * *